(12) United States Patent
Alouini et al.

(10) Patent No.: US 8,655,017 B2
(45) Date of Patent: Feb. 18, 2014

(54) METHOD FOR IDENTIFYING A SCENE FROM MULTIPLE WAVELENGTH POLARIZED IMAGES

(75) Inventors: Mehdi Alouini, Gosne (FR); Arnaud Beniere, Massy (FR); Daniel Dolfi, Orsay (FR); Gérard Berginc, Thiais (FR); François Goudail, Palaiseau (FR)

(73) Assignees: Thales, Neuilly sur Seine (FR); Institut D'Optique, Palaiseau Cedex (FR)

( * ) Notice: Subject to any disclaimer, the term of this patent is extended or adjusted under 35 U.S.C. 154(b) by 118 days.

(21) Appl. No.: 13/319,077

(22) PCT Filed: May 3, 2010

(86) PCT No.: PCT/EP2010/055974
§ 371 (c)(1),
(2), (4) Date: Mar. 9, 2012

(87) PCT Pub. No.: WO2010/128014
PCT Pub. Date: Nov. 11, 2010

(65) Prior Publication Data
US 2012/0183175 A1 Jul. 19, 2012

(30) Foreign Application Priority Data

May 7, 2009 (FR) ..................................... 09 02227

(51) Int. Cl.
*G06K 9/62* (2006.01)
(52) U.S. Cl.
USPC ........................................................ 382/103
(58) Field of Classification Search
None
See application file for complete search history.

(56) References Cited

U.S. PATENT DOCUMENTS

| | | |
|---|---|---|
| 5,235,463 A | 8/1993 | Broussoux et al. |
| 5,298,740 A | 3/1994 | Ayral et al. |
| 5,307,306 A | 4/1994 | Tournois et al. |
| 5,428,697 A | 6/1995 | Dolfi et al. |
| 5,430,454 A | 7/1995 | Refregier et al. |
| 5,475,525 A | 12/1995 | Tournois et al. |
| 5,936,484 A | 8/1999 | Dolfi et al. |

(Continued)

OTHER PUBLICATIONS

Snapshot Active Polarimetric and Multispectral Laboratory Demonstrator. Apr. 2009. Arnaud Bénièrea, Mehdi Alouinia, François Goudail, Arnaud Grisarda, Jérôme Bourderionneta, Daniel Dolfia, Ivar Baarstadd, Trond Løked, Peter Kaspersend, Xavier Normandine and Gerard Berginec.*

(Continued)

*Primary Examiner* — Stephen R Koziol
*Assistant Examiner* — Delomia Gilliard
(74) *Attorney, Agent, or Firm* — Baker & Hostetler LLP

(57) ABSTRACT

Techniques for identifying images of a scene including illuminating the scene with a beam of 3 or more wavelengths, polarized according to a determined direction; simultaneously acquiring for each wavelength an image $X_{//}(\lambda_i)$ polarized according to said direction and an image $X_\perp(\lambda_i)$ polarized according to a direction perpendicular to said direction, $X_\perp(\lambda_i)$ being spatially distinct from $X_{//}(\lambda_i)$; calculating for each wavelength an intensity image which is a linear combination of $X_{//}(\lambda_i)$ and $X_\perp(\lambda_i)$, providing an intensity spectrum for each pixel; calculating for each wavelength a polarization contrast image on the basis of an intensity ratio calculated as a function of $X_{//}(\lambda_i)$ and of $X_\perp(\lambda_i)$, providing a polarization contrast spectrum for each pixel; and calculating a spectro-polarimetric contrast image of the scene, each pixel of this spectro-polarimetric contrast image calculated based on the intensity spectrum and the contrast spectrum of the pixel considered.

14 Claims, 5 Drawing Sheets

(56) References Cited

U.S. PATENT DOCUMENTS

| | | | |
|---|---|---|---|
| 5,950,237 | A | 9/1999 | Micheron et al. |
| 6,313,792 | B1 | 11/2001 | Merlet et al. |
| 6,476,948 | B1 | 11/2002 | Canal et al. |
| 6,531,699 | B1 | 3/2003 | Micheron et al. |
| 7,016,040 | B2 | 3/2006 | Chen et al. |
| 7,271,386 | B2 | 9/2007 | Lawrence et al. |
| 2004/0047533 | A1 | 3/2004 | Huignard |
| 2005/0141900 | A1 | 6/2005 | Pochelle et al. |
| 2005/0264813 | A1* | 12/2005 | Giakos .......................... 356/369 |
| 2007/0241267 | A1* | 10/2007 | Gruev et al. .................. 250/225 |
| 2008/0055700 | A1 | 3/2008 | Bourderionnet et al. |
| 2008/0283752 | A1 | 11/2008 | Czarny et al. |
| 2009/0225800 | A1 | 9/2009 | Alouini et al. |
| 2010/0039646 | A1 | 2/2010 | Bourderionnet et al. |
| 2010/0039650 | A1 | 2/2010 | Molin et al. |
| 2010/0123901 | A1 | 5/2010 | Schwartz et al. |
| 2010/0213356 | A1 | 8/2010 | Berginc et al. |
| 2010/0271475 | A1* | 10/2010 | Schwiegerling et al. ..... 348/135 |
| 2011/0019179 | A1 | 1/2011 | Molin et al. |
| 2011/0019906 | A1 | 1/2011 | Berginc et al. |
| 2011/0122417 | A1 | 5/2011 | Molin et al. |
| 2011/0254924 | A1 | 10/2011 | Berginc et al. |

OTHER PUBLICATIONS

Multispectral Polarimetric Imaging with Coherent Illumination: Towards Higher Image Contrast. Apr. 2004. Mehdi Alouini, François Goudail, Philippe Réfrégier, Arnaud Grisard, Eric Lallier and Daniel Dolfi.*

A.R. Harvey et al.: "Spectral Imaging in a Snapshot," Spectral Imaging: Instrumentation, Applications, and Analysis III, Proceedings of SPIE, vol. 5694, 2005.

S.A. Mathews: "Design and fabrication of a low-cost, multispectral imaging system," Applied Optics, vol. 47, No. 28, Oct. 1, 2008.

H. Sauer et al.: "Accurate modeling of optical system aberrations applied to the design of a stationary Fourier transform spectroradiometer," Optical Design and Engineering II, Proceedings of SPIE vol. 5962, 596212 (2005).

R.G. Vaughan et al.: "Synthesis of High-Spatial Resolution Hyperspectral VNIR/SWIR and TIR Image Data for Mapping Weathering and Alteration Minerals in Virginia City, Nevada," Geoscience and Remote Sensing Symposium, IGARSS '04. Proceedings. 2004 IEEE International, pp. 1296-1299 (2004).

M.F. Noomen: "Hyperspectral reflectance of vegetation affected by underground hydrocarbon gas seepage," International Institute for Geo-information Science & Earth Observation, 2007.

N. Kosaka et al.: "Forest Type Classification Using Data Fusion of Multispectral and Panchromatic High-Resolution Satellite Imageries," Geoscience and Remote Sensing Symposium, IGARSS '05. Proceedings. 2005 IEEE International, 2005, pp. 2980-2983 (2005).

S. Schilders et al.: "Resolution improvement in microscopic imaging through turbid media based on differential polarization gating," Applied Optics, vol. 37, No. 19, Jul. 1, 1998.

P. Terrier et al.: "Segmentation of rough surfaces using a polarization imaging system," J. Opt. Spc. Am. A, Optical Society of America, vol. 25, No. 2, pp. 423-430, Feb. 2008.

D.T. Cassidy et al.: "Strain mapping by measurement of the degree of polarization of photoluminescence," Applied Optics, vol. 43, No. 9, pp. 1811-1818, Mar. 20, 2004.

M. Anastasiadou et al.: Polarimetric imaging for the diagnostic of cervical cancer, phys. stat. col. (c), vol. 5, No. 5, pp. 1423-1426, (2008).

L. Le Hors et al.: "A phenomenological model of paints for multispectral polarimetric imaging," Targets and Backgrounds VII: Characterization and Representation, Proceedings of SPIE vol. 4370, pp. 94-105, (2001).

L. Le Hors et al.: "Multispectral polarization active imager in the visible band," Laser Radar Technology and Applications V, Proceedings of SPIE, vol. 4035, pp. 380-389, (2000).

Beniere A. et al.: "Snapshot active polarimetric and multispectral laboratory demonstrator," Laser Radar Technology and Applications xiv Apr. 15-16, 2009 Orlando, FL, USA, vol. 7523, May 2, 2009.

Yong-Qiang Zhao et al.: "Object Detection by Spectropolarimeteric Imagery Fusion," IEEE Transactions on Geoscience and Remote Sensing, IEEE Service Center, Piscataway, NJ, US, vol. 46, No. 10, Oct. 1, 2008, pp. 3337-3345.

Mehdi Alouini et al.: "Multispectral polarimetric imaging with coherent illumination: towards higher image contrast," Polarization: Measurement, Analysis, and Remote Sensing VI Apr. 15, 2004 Orlando, FL, USA, vol. 5432, No. 1, 2004, pp. 133-144.

* cited by examiner

METHOD FOR IDENTIFYING A SCENE FROM MULTIPLE WAVELENGTH POLARIZED IMAGES

CROSS-REFERENCE TO RELATED APPLICATIONS

This application is a National Stage of International patent application PCT/EP2010/055974, filed on May 3, 2010, which claims priority to foreign French patent application No. FR 09 02227, filed on May 7, 2009, the disclosures of each of which are incorporated by reference in their entireties.

FIELD OF THE DISCLOSED SUBJECT MATTER

The field of the invention is that of the identification of the nature of the material of an object and of its surface state.

BACKGROUND

This identification is often achieved by multispectral imaging; the latter is based on a spectral decomposition of each point of the observed scene.

Accordingly, there exist several techniques. The most widespread implement a spectro-imager or colored filters. Other much less commonplace techniques use a Fourrier transform spectrometer to obtain the spectral decomposition. Multispectral and hyperspectral imagers operate mainly in passive mode: the light backscattered by the scene originates from solar or infrared radiation, from the inherent emission of the objects of the scene. Multispectral imaging covers a wide field of applications. It is used in geology for the identification of certain minerals and in particular for the detection of precious metals. It is also of interest in the oil industry for the detection of hydrocarbon and gas traces by direct observation or by observation of their effects on vegetation. In the field of agriculture, multispectral imaging makes it possible to track the development of plantations, to detect the presence of parasites or to evaluate the level of irrigation. It should be noted that multispectral imaging is penetrating ever more into ecological fields for the effective tracking of deforestation or reforestation of the terrestrial surface for example. These imagers are often carried aboard observation airplanes or satellites. The Landsat satellites, for example, carry 7 radiometers on board. It may be noted finally that multispectral imaging is beginning to find applications in the field of defense and security for zone monitoring notably. Its main objective is to circumvent the camouflage measures taken by the military in the visible and thermal regions of the optical spectrum. In this approach, one in fact gambles that the spectral analysis band is sufficiently large and resolved for each object to have a unique signature.

Although less widespread, it is known to resort to monochromatic polarimetric imaging for applications in microscopy, in the characterization of surfaces or interfaces, in the detection of stresses and in biology for tracking the evolution of cancerous cells for example. This type of imaging makes it possible to analyze the state of polarization of the light backscattered by an object. Polarimetric imagers often operate in active mode. A system which comprises a laser source illuminating the scene of interest and a detection system sensing the laser flux back-scattered by the scene and making it possible to form a two-dimensional image is called an active imager. It is necessary to fix or to control the state of polarization of the illumination light.

There exist diverse acquisition procedures. The most exhaustive is Muller imaging in which the state of polarization of the backscattered light is analyzed in a rigorous manner as a function of the state of polarization of the incident light. It requires the acquisition of 16 images, each associated with an element of the Muller matrix (4×4). Muller imaging is useful when the object to be characterized produces on the light, in addition to a pure depolarization, a change of polarization state due to a geometric, birefringence or optical activity effect. It finds applications in the biomedical field and in microscopy. More pragmatically, it is often sufficient to produce a polarimetric contrast image. In this case the state of polarization of the incident light is fixed (often a linear polarization) and the light backscattered by the object in accordance with a parallel polarization is analyzed; and then the light backscattered by the object in accordance with an orthogonal polarization is analyzed. Thus, the number of images to be acquired is limited to two without however losing an enormous amount of information, provided that the object analyzed is purely depolarizing. This is often the case when scenes on a human scale are considered.

In the foregoing, whether it is by multi-spectral imaging or by polarimetric imaging, the images are acquired sequentially over time.

These techniques are no longer efficacious if the imaged scene varies over time as for example in the cases of a scene which comprises objects in motion, or in the presence of atmospheric disturbances or else when the illumination of the scene is pulsed with energy fluctuations from one pulse to another.

SUMMARY

The aim of the invention is to alleviate these drawbacks.

The invention is based on the following property. Depending on the nature of the material, there exists a relationship between the intensity spectrum (also designated reflectance spectrum) and the spectrum of degree of polarization, which provides information about the nature of the object observed. This property is exploited to produce images of a new type called spectro-polarimetric correlation images or SPC images.

More precisely the subject of the invention is a method for identifying images of a scene which comprises a step of illuminating the scene with a beam of N wavelengths, polarized according to a determined direction, N being an integer greater than or equal to 3. It is mainly characterized in that it comprises the following steps:

simultaneous acquisition for each wavelength of an image polarized according to said direction, i.e. N images denoted $X_{//}(\lambda_i)$ with i varying from 1 to N and of an image polarized according to a direction perpendicular to said direction, i.e. N images denoted $X_\perp(\lambda_i)$, these images $X_\perp(\lambda_i)$ being spatially distinct from the images $X_{//}(\lambda_i)$, calculation for each wavelength, of an intensity image, which is a linear combination of $X_{//}(\lambda_i)$ and of $X_\perp(\lambda_i)$, to these N intensity images there therefore corresponding for each pixel an intensity spectrum, calculation for each wavelength, of a polarization contrast image on the basis of an intensity ratio calculated as a function of $X_{//}(\lambda_i)$ and of $X_\perp(\lambda_i)$, to these N polarization contrast images there therefore corresponding for each pixel a polarization contrast spectrum, calculation of an image of the scene termed a spectro-polarimetric contrast image and denoted SPC image, each pixel of this image being obtained on the basis of the intensity spectrum and of the contrast spectrum of the pixel considered.

This method makes it possible to obtain the information sought, with the help of images constructed on the basis of the degree of correlation between the intensity spectrum and the polarization spectrum.

It makes it possible to obtain the identifying information for a scene both in static and moving scenes, even in the presence of atmospheric turbulence. It circumvents the noise related to the temporal fluctuations in the illumination intensity and the statistics of the noise in the two N orthogonal images are the same.

The polarization contrast image is for example calculated as a function of $(X_{//}(\lambda_i) - X_\perp(\lambda_i))/(X_{//}(\lambda_i) + X_\perp(\lambda_i))$ or of $X_{//}(\lambda_i)/X_\perp(\lambda_i)$.

The intensity image is for example of the form $X_{//}(\lambda_i) + X_\perp(\lambda_i)$.

According to one characteristic of the invention, K other SPC images are respectively obtained on the basis of the intensity spectrum and of the contrast spectrum by K other calculations, and a new SPC image is obtained on the basis of these K SPC images ($K \geq 1$).

The SPC image may be obtained on the basis of a spectro-polarimetric graph SPG which comprises N points with coordinates $Ui=INT(\lambda_i)$ and $Vi=OSC(\lambda_i)$.

Various examples of modes of calculation, established on the basis of the following formulae, are proposed:

$INT(\lambda_i) = X_{//}(\lambda_i) + X_\perp(\lambda_i)$ and $OSC(\lambda_i) = (X_{//}(\lambda_i) - X_\perp(\lambda_i))/(X_{//}(\lambda_i) + X_\perp(\lambda_i))$.

According to a first mode of calculation, the SPC image is obtained by fitting the SPG with a decreasing exponential function.

According to a second mode of calculation, the SPC image is obtained by linear correlation of the SPG.

According to a third mode of calculation, the SPC image is obtained through a confidence index for the SPG.

According to a fourth mode of calculation, the SPC image is obtained through the ratio between the dispersion of the intensity spectrum and of the OSC spectrum According to one characteristic of the invention, the images $X_\perp(\lambda_i)$ and $X_{//}(\lambda_i)$ are interleaved.

The subject of the invention is also a system for identifying a scene which comprises means for implementing the method such as described above.

According to one characteristic of the invention, the implementation means comprise a device for illuminating the scene with a beam of N wavelengths, polarized according to a determined direction, a device for simultaneously acquiring the N images $X_{//}(\lambda_i)$, and the N images denoted $X_\perp(\lambda_i)$ and means for processing said images able to calculate an SPC image.

According to a particular embodiment, the acquisition device comprises a single detector.

BRIEF DESCRIPTION OF THE DRAWINGS

Other characteristics and advantages of the invention will become apparent on reading the detailed description which follows, given by way of nonlimiting example and with reference to the appended drawings in which.

Across figures, the same elements are tagged by the same references.

DETAILED DESCRIPTION

Figure 1:
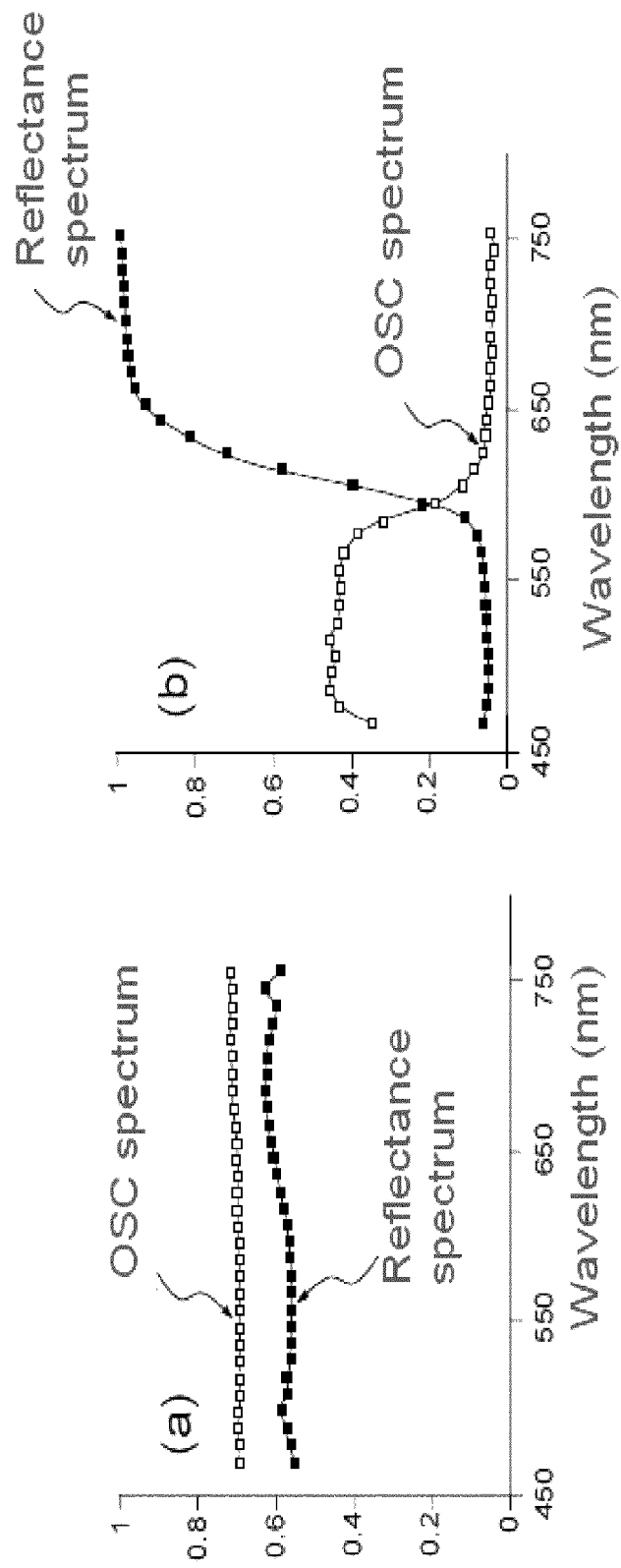
FIG. 1 schematically represents two examples of reflectance spectrum and OSC spectrum for a metal sheet (a) and for a red colored gauge (b), FIGS. 2a and 2b schematically represent a first exemplary configuration of a device for acquiring N images $X_{//}(\lambda_i)$ and N images $X_\perp(\lambda_i)$, using a Wollaston prism and one and the same detector (FIG. 2a) or a polarization-separating cube and two distinct detectors (FIG. 2b), FIGS. 3a and 3b schematically represent a second exemplary configuration of a device for acquiring N images $X_{//}(\lambda_i)$ and N images $X_\perp(\lambda_i)$, using a splitter plate and polarizers with (FIG. 3a) or without (FIG. 3b) intermediate image, FIG. 4 schematically represents a third exemplary configuration of a device for acquiring N images $X_{//}(\lambda_i)$ and N images $X_\perp(\lambda_i)$, using two distinct devices, FIG. 5 schematically represents a fourth exemplary configuration of a device for acquiring N images $X_{//}(\lambda_i)$ and N images $X_\perp(\lambda_i)$ that are interleaved, FIG. 6 schematically represents an example of INT and OSC images obtained with the imager described in relation with FIG. 2a, FIG. 7 schematically represents an exemplary spectro-polarimetric graph (SPG) represented by N (N=7) points with coordinates Ui and Vi, and the fitted merit function, for a pixel of an image of a red plastic.

The property exploited by the invention will first be explained.

Under monochromatic polarized illumination, the depolarization effects can be correlated with the surface roughness of the objects and their nature. It is known, for example, that metallic objects depolarize light less than scattering objects. It is thus possible to artificially increase the contrast of a metallic object in a natural scene. Accordingly, the scene is illuminated with polarized (linearly for example) light and two images with parallel polarization, $X_{//}$, and orthogonal polarization, $X_\perp$, are acquired. A contrast image, OSC "Orthogonal State Contrast", given by the formulation $OSC = (X_{//} - X_\perp)/(X_{//} + X_\perp)$ is thereafter calculated on the basis of these two images. However the use of a single wavelength is not sufficient to determine the nature of an object. Indeed, depending on the illumination wavelength, a scattering object, this time, may exhibit as high a degree of polarization as a metallic object. It is noted for example, that the degree of polarization of the light scattered by a metal sheet increases slightly with the wavelength since its apparent roughness decreases. This is no longer valid for scattering objects. It is possible to describe scattering objects as objects exhibiting a bigger incoherent scattered intensity than coherent scattered intensity. Thus, it is shown that paints of different colors, but exhibiting the same surface roughness, have different degrees of polarization. Moreover, their degree of polarization depends strongly on their color and on the illumination wavelength. In particular, it has been observed that the reflectance spectrum and OSC spectrum of these paints exhibit complementary profiles. To a certain extent this remains valid for other scattering objects such as plastic and natural objects.

To understand these observations, it is necessary to distinguish between surface effects and volume effects. If a scattering material is illuminated at a wavelength at which it absorbs, the little light that is backscattered originates from the surface interaction. It is therefore little depolarized. Conversely, if the same material is illuminated at a wavelength at which it does not absorb, the light then undergoes multiple volume scatterings. It is therefore strongly depolarized. The spectra of degree of polarization and of reflectance of a non-metallic object are therefore complementary, whereas they are not for a metallic material. In order to quantify these effects, the applicant has devised a phenomenological model. This model is based on separation of the surface contribution and volume contribution to the depolarization. The weak depolarization induced by the surface is related to the roughness and it depends on the roughness/wavelength ratio. Conversely, the depolarization induced by the volume interactions being related to the absorption of the material, it depends strongly on the illumination wavelength and may exhibit non-monotonic spectral variations.

According to the nature of the material, the relation which exists between the reflectance spectrum and the spectrum of degree of polarization therefore provides information about the nature of the object observed. Examples of reflectance and OSC spectra obtained for a metal sheet and a red colored gauge are shown FIG. 1.

It is this property which is exploited in the invention to produce images of a new type called spectro-polarimetric correlation images or SPC images.

In order to produce the SPC images, it is necessary firstly to illuminate the scene with a beam of N wavelengths, polarized according to a determined direction, and then on the one hand to have access, simultaneously and at any point of the image, to the two orthogonal polarization states, doing so at several wavelengths (N wavelengths $\lambda_i$, i varying from 1 to N) and on the other hand to analyze spectra of intensity and of degree of polarization.

The relevance of this analysis depends directly on the quality of measurement. The latter must therefore be as free as possible from the technical imperfections related to the sequential acquisition of the two polarization states.

The simultaneous acquisition of the 2 N polarized images is firstly considered.

According to a first embodiment, the images of the two orthogonal polarization states are formed simultaneously on the same detection matrix. Noise related to the temporal fluctuations in the illumination intensity is thus circumvented and the noise statistics in the two orthogonal images are guaranteed to be the same.

The difficulty is then to obtain on the detector two images which are free of aberrations.

Figure 2A:
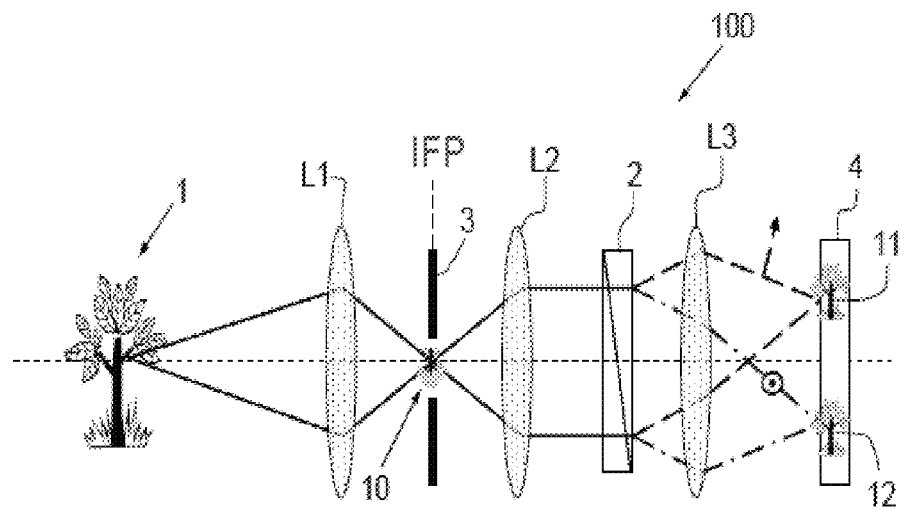

According to a first exemplary device 100, shown in FIG. 2a, for acquiring the 2N images of the scene 1, the spatial separation of the two polarization states is obtained with the aid of a Wollaston prism 2. As shown diagrammatically in this figure, an intermediate image 10 is produced by means of a first grouping of lenses L1, and is projected to infinity by means of a second grouping of lenses L2, before entering the Wollaston prism 2. A rectangular field mask 3 is arranged in the intermediate focal plane IFP where the intermediate image 10 is formed, so that the polarized images 11 and 12 respectively denoted $X_{//}(\lambda_i)$ and $X_{\perp}(\lambda_i)$ are exactly overlaid on one another on the detector 4. Once angularly separated, the two polarization states are imaged on the detection matrix 4 by means of a third grouping of lenses L3. This approach accords the spectro-polarimetric imager a sensitivity limit imposed by photon noise and no longer by the various imperfections and miscellaneous technical noise.

The optical design of this imager must be done with care so as to minimize at one and the same time the geometric and chromatic aberrations.

The N wavelengths can belong to the same visible spectral band, the very near infrared, near infrared, infrared or ultraviolet; they can also be extracted from various spectral bands.

Selection in terms of wavelength (or spectral selection) is obtained at the level of the detection matrix which may be trichromic (N=3), quadri-chromic (N=4) or more.

Spectral selectivity can also be obtained with a monochrome detection matrix, either by placing interferential filters in front of the entrance pupil, or by tuning the wavelength of the illumination source(s).

The N images $X_{//}(\lambda_i)$ may be spatially superimposed but not necessarily. Likewise for the images $X_{\perp}(\lambda_i)$.

This imager 100 may be provided in several variants according to the detection matrix used. It can thus cover the visible wavelength regions by using a color or monochrome Silicon based detection matrix, the very near infrared by using a detection matrix based on InGaAs, the near infrared by using a detection matrix based on HgCdTe and the near ultraviolet by using a matrix based on SiC, GaN or AlGaN.

Figure 2B:
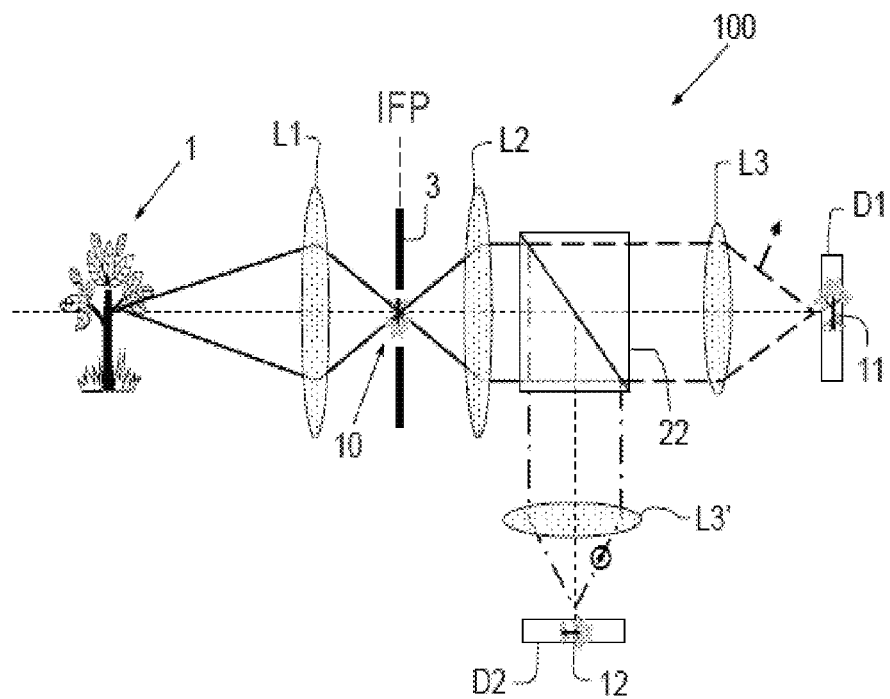

According to a variant, shown in FIG. 2b, of this first embodiment, the Wollaston prism is replaced with a polarization-separating cube 22. On exiting this cube 22, the two polarization states are spatially separated and are respectively imaged on two distinct matrix detectors D1 and D2 by means of the third groupings of lenses L3 and L3'.

Figure 3A:
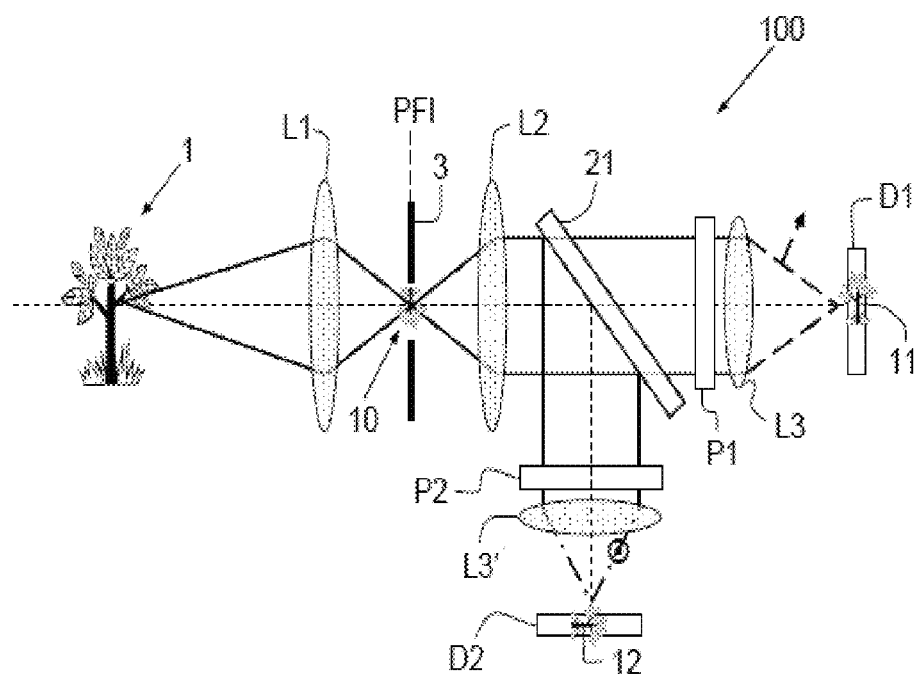

According to a second exemplary device 100, shown in FIG. 3a, for acquiring the 2N images, the spatial separation of the image is achieved with the aid of a splitter plate 21 arranged at the location of the Wollaston prism of the previous example. On a first pathway arising from this splitter plate 21 are arranged a polarizer P1 making it possible to obtain a first parallel polarization state, and then a third grouping of lenses L3 forming the N polarized images $X_{//}(\lambda_i)$ on a first detector D1; on the second pathway arising from this splitter plate 21 are arranged a polarizer P2 making it possible to obtain the perpendicular polarization state, and then a third grouping of lenses L3' forming the N polarized images $X_{\perp}(\lambda_i)$ on a second detector D2. The detectors D1 and D2 of the same type as that of the previous imager, are preferably identical.

Figure 3B:
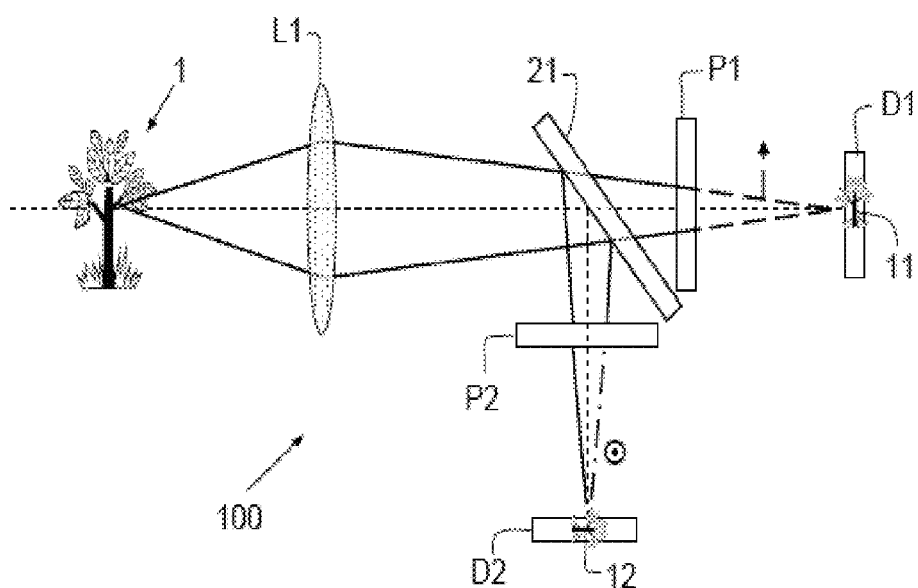

According to a variant, shown in FIG. 3b, of this second embodiment, no intermediate image is produced: the images are formed directly on the matrix detectors D1 and D2 by means of a first grouping of lenses L1. The groupings of lenses L2, L3 and L3' are not used.

Figure 4:
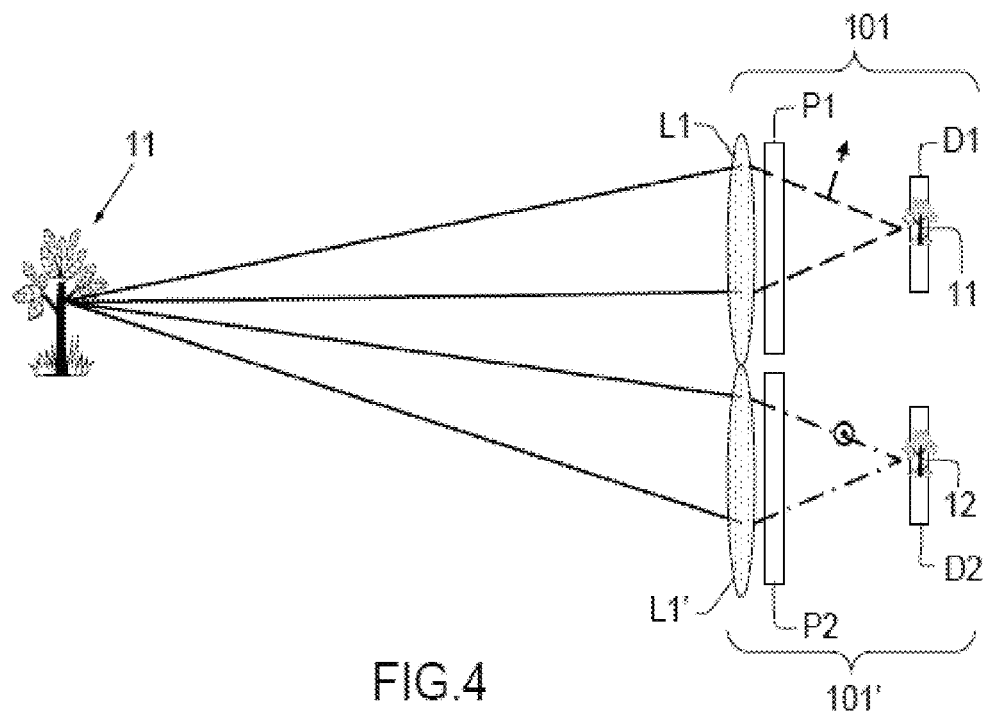

According to a third exemplary device, shown in FIG. 4, for acquiring the 2N images, the spatial separation of the image is achieved by two distinct imaging devices 101, 101', each of these devices comprising a grouping of lenses L1, L1' supplemented with a polarizer P1, P1' and a detector D1, D1' on which the grouping of lenses L1, L1' forms the image of the scene 1. Each imager 101, 101' sees the scene from a slightly different angle, this having no negative consequence when the scene is sufficiently distant.

Figure 5:
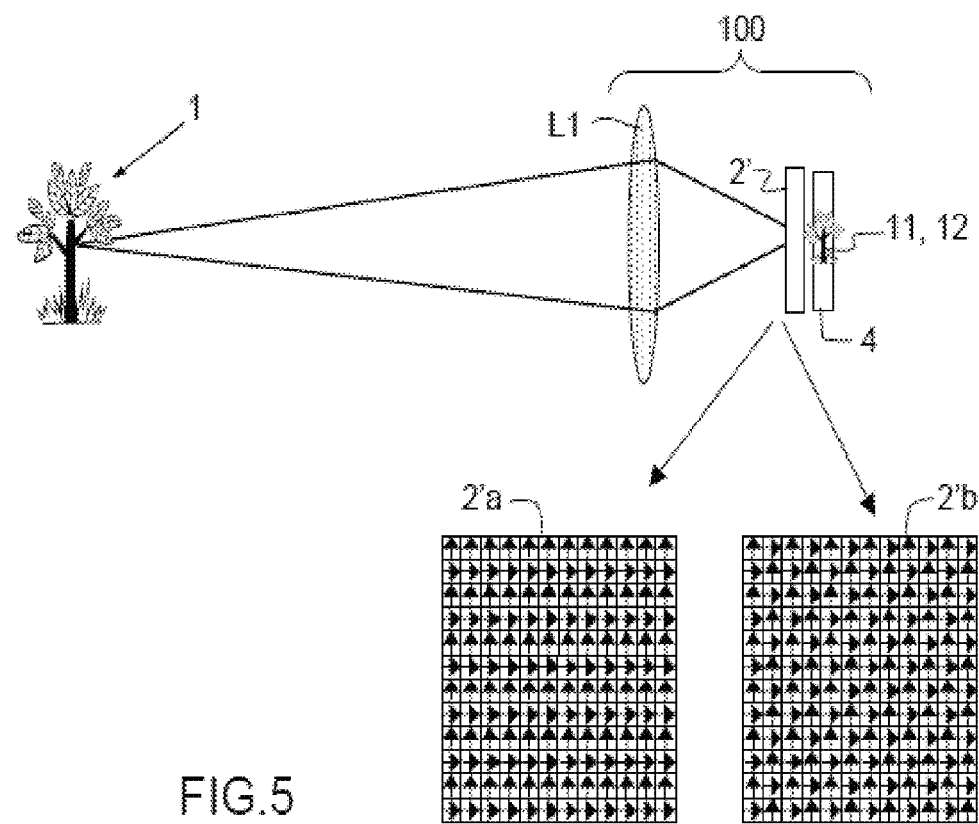

It is also possible to use an imager forming on one and the same detector interleaved images $X_{//}(\lambda_i)$ and $X_{\perp}(\lambda_i)$, of which an exemplary architecture is shown in FIG. 5. The images $X_{//}(\lambda_i)$ and $X_{\perp}(\lambda_i)$ (denoted 11 and 12) of the scene 1 are formed on a detector 4 by means of a grouping of lenses L1, the spatial separation of the images being obtained by their interleaving. Accordingly, a grid 2' of elementary polarizers is placed just in front of the detector 4. Each elementary polarizer is of the size of a pixel of the detector, the polarization of a row (or of a column) of elementary polarizers being alternated with that of the neighboring row (or column) as illustrated on the polarizer seen front-on of reference 2'a or else, the polarization of one being alternated with that of its neighbor as illustrated on the polarizer seen front-on of reference 2'b.

On completion of this step, by virtue of one of these imagers, two images have therefore been acquired at each wavelength λi: hence 2N polarized images have been acquired. The first N images $X_{//}(\lambda_i)$ correspond to the polarization state parallel to that of the illumination. The second N images dubbed $X_{\perp}(\lambda_i)$ correspond to the polarization state orthogonal to that of the illumination.

For each point of the scene (each pixel) these 2N measurements are used to ultimately obtain a new contrast image, by performing the following step.

The step of processing the 2N acquired images is now considered, which relies on the joint utilization of the reflectance spectrum (also designated intensity spectrum) and of the spectrum of degree of polarization (or polarimetric spectrum, OSC spectrum).

On the basis of these two N acquired images we calculate for each of the N wavelengths $\lambda 1, \ldots, \lambda i, \ldots \lambda N$ available:
- an intensity INT image($\lambda i$) on the basis of a linear combination of the polarized images, which relates to the reflectance of the observed object and,
- a polarization contrast image also designated OSC image ($\lambda i$) the acronym standing for the expression "Orthogonal State Contrast", established on the basis of an intensity images ratio calculated as a function of the polarized images.

The linear combination is for example of the form:

$$INT(\lambda_i) = (X_{//}(\lambda_i) + X_{\perp}(\lambda_i)),$$

and the polarization contrast image is for example of the form:

$$OSC(\lambda_i) = (X_{//}(\lambda_i) - X_{\perp}(\lambda_i))/(X_{//}(\lambda_i) + X_{\perp}(\lambda_i)).$$

Figure 6:
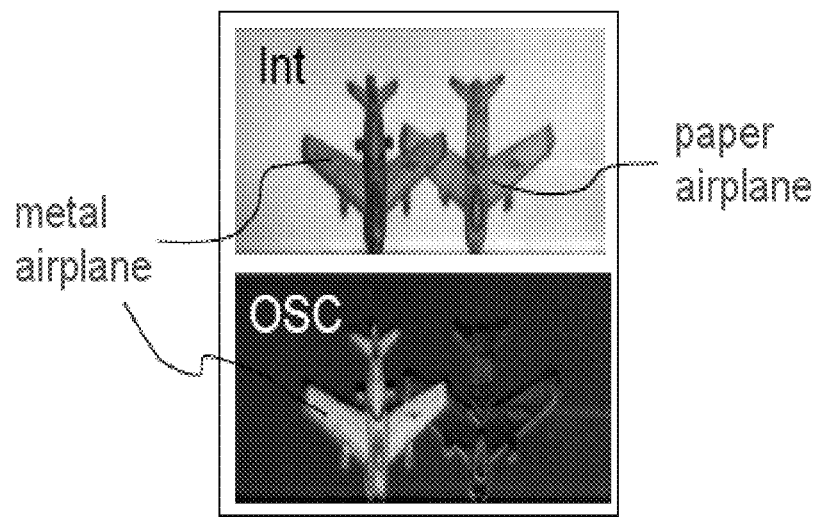

An example of such INT and OSC images obtained with the imager described in relation with FIG. 2a is seen FIG. 6. The scene comprises two airplanes, one made of paper, the other of metal. The INT and OSC images are obtained in a single acquisition: the OSC image makes it possible to distinguish on the basis of the two a priori identical airplanes visible on the INT image, the nature of the material which differs from one airplane to the other.

The INT images can also be of the form:

$$INT = (X_{//} + X_{\perp})/\max(X_{//} + X_{\perp}), \text{ the values of the INT images then lying between 0 and 1; or}$$

$$INT = 2(X_{//} + X_{\perp}).$$

The OSC images can also be of the form:

$$OSC = \log[(X_{//} - X_{\perp})/(X_{//} + X_{\perp})] \text{ or}$$

$$OSC = \log[(X_{//}/X_{\perp})] \text{ or}$$

$$OSC = X_{//}/X_{\perp}.$$

For each of the points of the scene, and therefore for each pixel of the INT and OSC images, an intensity spectrum is then calculated on the basis of the N intensity images INT and an OSC spectrum is calculated on the basis of the N polarization contrast images OSC. The spectra are in practice vectors of size N, that is to say corresponding to the N different wavelengths ($\lambda 1, \lambda 2 \ldots \lambda N$). The intensity spectrum is denoted U and the OSC spectrum is denoted V. Thus U and V are vectors of size N such that $U_i = INT(\lambda_i)$ and $V_i = OSC(\lambda_i)$.

It is possible in the course of this step to use a calculation tool which is a spectro-polarimetric graph or "SPG". It is not necessary but it allows a visual representation. The SPG is a cluster of N points whose coordinates are Ui and Vi. A generalization consists in plotting fi(U) and gi(V), where fi and gi are functions; they may allow normalization or differentiation for example.

On the basis of this graph, it is possible to extract several quantities, designated SPC images, relating to the correlation existing between the intensity spectrum and the OSC spectrum. These SPC images may be obtained without resorting to the SPG graph, directly on the basis of the 2N images by means of a mathematical formula tailored to each case.

Various examples will now be given of obtaining a final SPC image on the basis of such a graph and with:

$$INT(\lambda_i) = (X_{//}(\lambda_i) + X_{\perp}(\lambda_i))$$

and $OSC(\lambda_i) = (X_{//}(\lambda_i) - X_{\perp}(\lambda_i))/(X_{//}(\lambda_i) + X_{\perp}(\lambda_i)).$ According to a first example, the SPC image is obtained by fitting the SPG with a decreasing exponential. Studies conducted by the applicant have made it possible to show that the OSC decreases exponentially with reflectance for scattering materials. The Spectro Polarimetric Graph of scattering materials can therefore be modeled by a function of the type:

$$\phi(Ui) = a \exp(-b*Ui) + c.$$

For each of the points of the image, the parameters a, b and c are optimized so that the function $\phi$ best approximates the measured points. Accordingly, use is made of a merit function f_merit that one seeks to minimize by conventional optimization schemes.

In our case:

$$f_{merit} = \sum_{i=1}^{N} |V_i - \Phi(U_i)|^2$$

Figure 7:
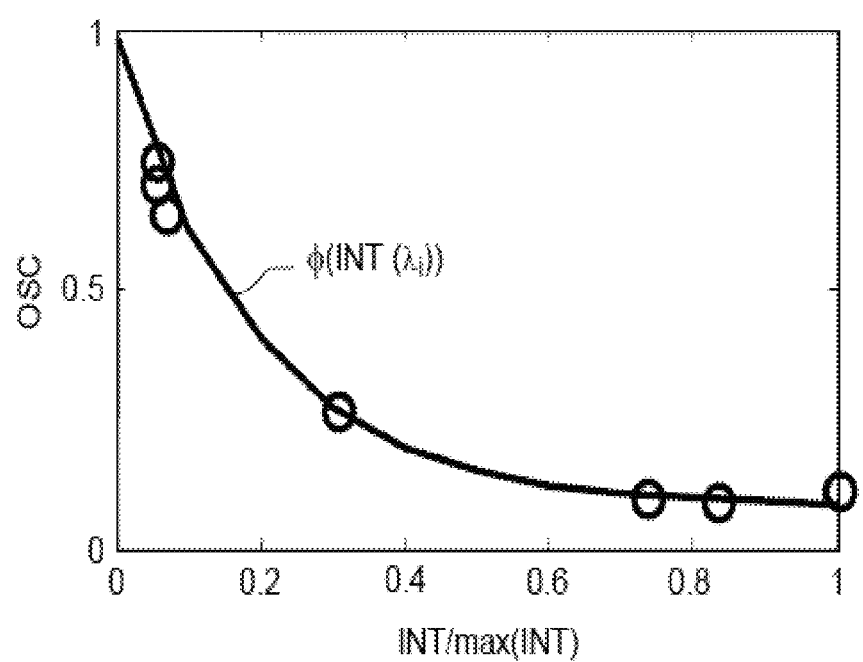

The SPC image is this function $\phi$ obtained by the optimized merit function. For each pixel of the SPC image we have a value of $\phi$ and a value for the three parameters a,b,c an example of which, obtained for a pixel of an image of a red plastic, is shown in FIG. 7. The model is tailored to scattering materials. The SPG of the metal sheet cannot be fitted well by such a function. Its merit function is high. Conversely, the model makes it possible to reliably estimate the behavior of the paper which is scattering. Its merit function is lower.

In a second example, the SPC image is obtained by linear correlation of the SPG. Prompted by the previous scheme, the exponential decay of the OSC image with the reflectance image is exploited. The coefficient of linear correlation between INT and −log(OSC) is for example calculated for each point (pixel) of the image. The linear correlation coefficient may be estimated by Pearson's correlation coefficient defined by:

$$\rho(U, V) = \frac{1}{N-1} \sum_{i=1}^{N} \left(\frac{U_i - \overline{U}}{\sigma_U}\right)\left(\frac{V_i - \overline{V}}{\sigma_V}\right) \text{ with}$$

$$\overline{U} = \frac{1}{N}\sum_{i=1}^{N} U_i \text{ and } \sigma_U = \sqrt{\frac{1}{N-1}\sum_{i=1}^{N}(U_i - \overline{U})^2}$$

$$\overline{V} = \frac{1}{N}\sum_{i=1}^{N} V_i \text{ and } \sigma_V = \sqrt{\frac{1}{N-1}\sum_{i=1}^{N}(V_i - \overline{V})^2}$$

This quantity relates to the correlation between the spectra. It is called the correlation of order 0.

In the same manner it is possible to calculate the coefficient of correlation between the slopes of the spectra, that is to say between the random variables $$U'_i = \frac{INT(\lambda_{i+1}) - INT(\lambda_i)}{\lambda_{i+1} - \lambda_i} \text{ and } V'_i = \frac{OSC(\lambda_{i+1}) - OSC(\lambda_i)}{\lambda_{i+1} - \lambda_i}$$

this being called the correlation of order 1.

In the same manner it is possible to calculate the correlations of order 2, 3 . . . N. For highly scattering red plastic the SPC image which is the image of order 0 correlation between INT and −log(OSC) appears white. Its intensity spectrum and OSC spectrum are indeed highly correlated. The metal for its part appears black with a correlation coefficient of nearly 0.

In a third example, the SPC image is obtained by the confidence index for the SPG: the confidence index makes it possible to indicate whether the correlation measurement is reliable. This index is equal to the spectral variance of the intensity, divided by the spectral average of the intensity:

$$IND_{INT} = \frac{\sqrt{\frac{1}{N}\sum_{i=1}^{N} U_i^2 - \left(\frac{1}{N}\sum_{i=1}^{N} U_i\right)^2}}{\frac{1}{N}\sum_{i=1}^{N} U_i}$$

or to the spectral variance of the OSC, divided by the spectral average of the OSC:

$$IND_{OSC} = \frac{\sqrt{\frac{1}{N}\sum_{i=1}^{N} V_i^2 - \left(\frac{1}{N}\sum_{i=1}^{N} V_i\right)^2}}{\frac{1}{N}\sum_{i=1}^{N} V_i}$$

Indeed if the reflectance spectrum (or the OSC spectrum) is highly dispersed, the corresponding points are far apart from one another, thereby making it possible to perform a fit or to calculate a correlation coefficient with greater accuracy.

In this fourth example, the SPC image is obtained by the relative dispersion of the spectra. The dispersion of the points of the SPG in the horizontal direction (which corresponds to the dispersion of the intensity spectrum) may be characterized by the variance of the vector U and the dispersion in the vertical direction (which corresponds to the dispersion of the OSC spectrum) may be characterized by the variance of the associated vector V. It is possible to effect the image of the ratio between these two variances:

$$DISP = \frac{\frac{1}{N}\sum_{i=1}^{N} U_i^2 - \left(\frac{1}{N}\sum_{i=1}^{N} U_i\right)^2}{\frac{1}{N}\sum_{i=1}^{N} V_i^2 - \left(\frac{1}{N}\sum_{i=1}^{N} V_i\right)^2}$$

This ratio will be large if the point cluster corresponding to the SPG is horizontally extensive and small if the point cluster is vertically extensive.

The SPC image obtained makes it possible to distinguish between a smooth and rough scattering material. Smooth plastic appears darker.

It is of course possible to produce several SPC images and to choose the best, that is to say the one which provides the most information sought, or indeed even to combine them to produce a new SPC image.

This processing of the acquired images is for example carried out in a conventional manner by image processing software.

The invention claimed is:

1. A method for identifying images of a scene, the method comprising:
    illuminating the scene with a beam of N wavelengths, polarized according to a determined direction, N being an integer greater than or equal to 3;
    simultaneously acquiring for each wavelength an image $X_{//}(\lambda_i)$ polarized according to said direction and an image $X_\perp(\lambda_i)$ polarized according to a direction perpendicular to said direction, these images $X_\perp(\lambda_i)$ being spatially distinct from the images $X_{//}(\lambda_i)$;
    calculating for each wavelength an intensity image which is a linear combination of $X_{//}(\lambda_i)$ and $X_\perp(\lambda_i)$, these N intensity images providing for each pixel an intensity spectrum;
    calculating for each wavelength a polarization contrast image on the basis of an intensity ratio calculated as a function of $X_{//}(\lambda_i)$ and of $X_\perp(\pi_i)$, these N polarization contrast images providing for each pixel a polarization contrast spectrum; and
    calculating a spectro-polarimetric contrast image of the scene, each pixel of this spectro-polarimetric contrast image calculated based on the intensity spectrum and the contrast spectrum of the pixel considered.

2. The method for identifying a scene according to claim 1, wherein the polarization contrast image is calculated as a function of $(X_{//}(\lambda_i) - X_\perp(\lambda_i))/(X_{//}(\lambda_i) + X_\perp(\lambda_i))$.

3. The method for identifying a scene according to claim 1, wherein the polarization contrast image is calculated as a function of $X_{//}(\lambda_i)/X_\perp(\lambda_i)$.

4. The method for identifying a scene according to claim 1, wherein the intensity image is of the form $X_{//}(\lambda_i) + X_\perp(\lambda_i)$.

5. The method for identifying a scene according to claim 1, wherein
    K other spectro-polarimetric contrast images are respectively obtained on the basis of the intensity spectrum and of the contrast spectrum by K other calculations, and in that
    a new spectro-polarimetric contrast image is obtained on the basis of these K spectro-polarimetric contrast images, K being an integer greater than or equal to 1.

6. The method for identifying a scene according to claim 1, characterized in that the spectro-polarimetric contrast image is obtained on the basis of a spectro-polarimetric graph comprising N points with coordinates Ui=INT($\lambda_i$) and Vi=OSC($\lambda_i$).

7. The method for identifying a scene according to claim 6, wherein
    the polarization contrast image is calculated as a function of $(X_{//}(\lambda_i) - X_\perp(\lambda_i))/(X_{//}(\lambda_i) + X_\perp(\lambda_i))$;
    the intensity image is of the form $X_{//}(\lambda_i) + X_\perp(\lambda_i)$; and
    the spectro-polarimetric contrast image is obtained by fitting the spectro-polarimetric graph with a decreasing exponential function.

8. The method for identifying a scene according to claim 6, wherein
    the polarization contrast image is calculated as a function of $(X_{//}(\lambda_i) - X_\perp(\lambda_i))/(X_{//}(\lambda_i) + X_\perp(\lambda_i))$;
    the intensity image is of the form $X_{//}(\lambda_i) + X_\perp(\lambda_i)$; and
    the spectro-polarimetric contrast image is obtained by linear correlation of the spectro-polarimetric graph.

9. The method for identifying a scene according to claim 6, characterized in that
   the polarization contrast image is calculated as a function of $(X_{//}(\lambda_i)-X_\perp(\lambda_i))/(X_{//}(\lambda_i)+X_\perp(\lambda_i))$;
   the intensity image is of the form $X_{//}(\lambda_i)+X_\perp(\lambda_i)$; and
   the spectro-polarimetric contrast image is obtained through a confidence index for the spectro-polarimetric graph.

10. The method for identifying a scene according to claim 6, characterized in that
   the polarization contrast image is calculated as a function of $(X_{//}(\lambda_i)-X_\perp(\lambda_i))/(X_{//}(\lambda_i)+X_\perp(\lambda_i))$;
   the intensity image is of the form $X_{//}(\lambda_i)+X_\perp(\lambda_i)$; and
   the spectro-polarimetric contrast image is obtained through a ratio between a dispersion of the intensity spectrum and of an orthogonal state contrast spectrum.

11. The method for identifying a scene according to claim 1, wherein the images $X_\perp(\lambda_i)$ and $X_{//}(\lambda_i)$ are interleaved.

12. A system for identifying a scene comprising means for implementing the method according to claim 1.

13. The system for identifying a scene according to claim 12, wherein the means for implementing the method comprises
   a device for illuminating the scene with a beam of N wavelengths, polarized according to a determined direction;
   a device for simultaneous acquisition of the N images denoted $X_{//}(\lambda_i)$, and of the N images denoted $X_\perp(\lambda_i)$; and
   means for processing said acquired images to calculate a spectro-polarimetric contrast image.

14. The system for identifying a scene according to claim 13, wherein the acquisition device comprises a single detector.

* * * * *

UNITED STATES PATENT AND TRADEMARK OFFICE
CERTIFICATE OF CORRECTION

PATENT NO. : 8,655,017 B2  Page 1 of 1
APPLICATION NO. : 13/319077
DATED : February 18, 2014
INVENTOR(S) : Alouini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 244 days.

Signed and Sealed this

Twenty-ninth Day of September, 2015

Michelle K. Lee
*Director of the United States Patent and Trademark Office*